May 21, 1946. C. J. VAN BOURGONDIEN Plant Pat. 691
FREESIA PLANT
Filed June 11, 1945
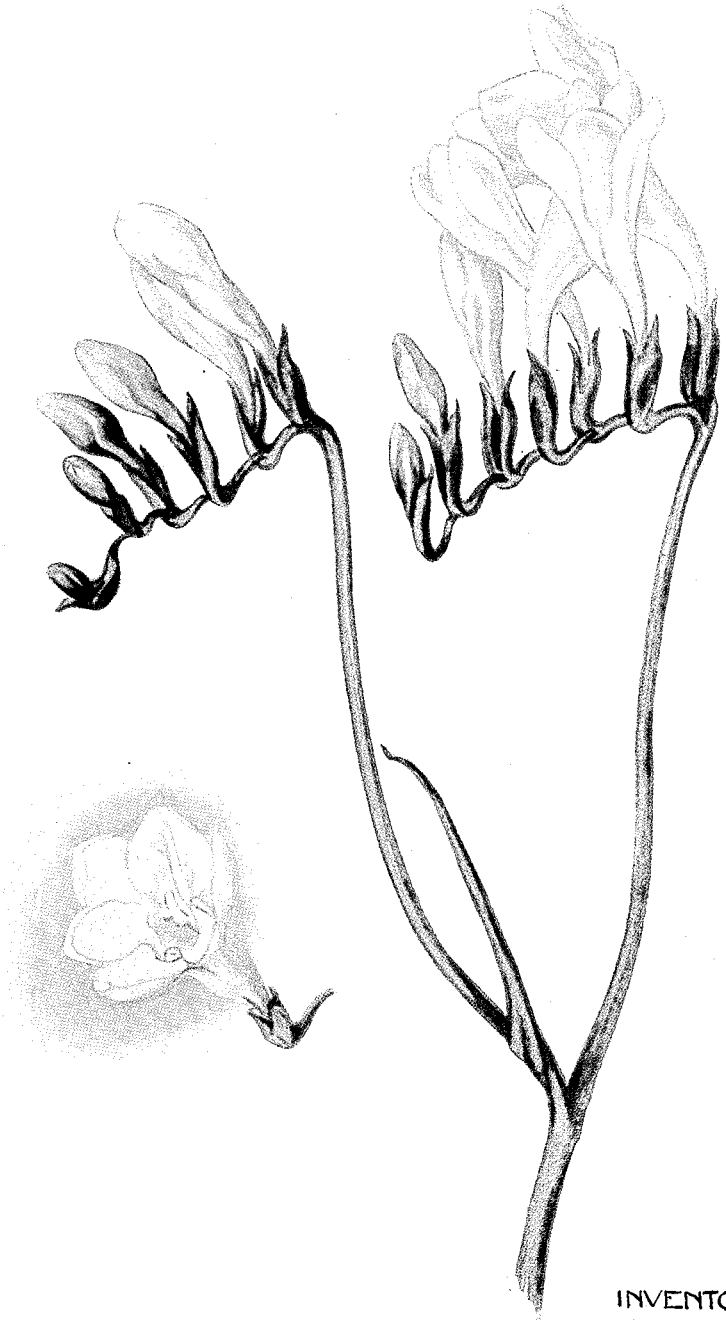
INVENTOR
Cornelius John Van Bourgondien
By Orville M. Kile
PLANT PATENT AGENT Patented May 21, 1946

Plant Pat. 691

UNITED STATES PATENT OFFICE

691

FREESIA PLANT

Cornelius John Van Bourgondien, Babylon, N. Y.,
assignor to Raymond Wilson, Carlsbad, Calif.

Application June 11, 1945, Serial No. 598,796

1 Claim. (Cl. 47—60)

My present invention relates to improvements in freesias, particularly those of the "giant" type. Its flower is primarily white and has a very heavy fragrance, as well as other desirable characteristics.

This new variety is the result of definite breeding efforts carried on by me at my greenhouses and has been further developed by selection in Southern California. It is a cross between the variety Albatre Supreme as the female parent and the variety Fairy as the male parent.

It has an early blooming season, is a very vigorous grower, and produces many large substantial flowers. Foliage is shorter than the flower stems, thus allowing greater ease in cutting the flowers. Asexual production by natural increase has proved the qualities of the variety to be firmly fixed.

Accompanying illustrations show a spike of blossoms of my new variety, indicating the usual number of blossoms open at one time.

Following is a detailed description of my new variety, in which color plate references indicate Ridgway's Color Standards and Nomenclature.

*The plant*

Growth: Healthy and vigorous. Height of foliage when grown outdoors averages 12 inches for bulb stock. When forced in a greenhouse, it attains a height of 24 to 30 inches.

Blooming habit: Prolific producer of large flowers held high above the foliage. Each spike has 3 or 4 flowers open at one time.

Blooming season: Early. In an average year, the variety blooms from February 15th to March 15th when grown outdoors in southern California. When grown in greenhouses the season is from about January 10th to March 15th.

Foliage: Heavy, dark green foliage, averaging 6 inches shorter than the flower stem. Leaves are ½ inch wide at broadest part, tapering to a point.

Stems: Very straight, thick and rigid. Approximately Oil Green (Plate V); tall, averaging 16 inches when grown in the open ground.

*The flower*

Bud: Long; slender. Smaller buds approximately Lettuce Green (Plate V). Just before opening, buds are greenish white sometimes with traces of violet.

Flower:

*Arrangement.*—Flowers are borne in spikes and along a jointed rachis which extends from the stem at an angle of about 40 degrees or less. Spikes have an average of 6 to 8 nicely placed blooms and buds with as many as four open and fresh at one time. Flowers are long and set far enough apart on the rachis to avoid a crowded appearance.

*Form.*—Tubular, with six overlapping petals or lobes which open out rather wide at the top.

*Petals.*—Six; smoothly rounded; slightly overlapping; texture heavy.

*Size.*—Very large. Average length of tube is 3 inches and average width is 1½ inches for outdoor growth.

*Color.*—Inner surface white with a deep cream overcast. Throat and large splotch on lower petal are a vivid yellow, approximately Light Cadmium (Plate IV), diminishing to Lemon Chrome (Plate IV) at edges of splotch. Outer surface of open flower is cream color with a slight greenish cast. The yellow of the throat and splotch show through to the outside of the translucent tube, producing Primuline Yellow (Plate XVI) at these points. Older flowers often have markings of violet near the base.

*Fragrance.*—Heavy.

*Bracts.*—Very large and substantial. Slightly darker green than the stems.

*Keeping qualities.*—Flowers keep unusually well, due at least in part to their substantial texture.

*Reproductive organs.*—Stamens and pistils cling close to upper petal or lobe. *Stamens* are three, large and pure white. *Pistil* is likewise pure white in newly opened flowers but sometimes mauve in older flowers. Pistil is divided into six branches at the top, and is larger than usually found in freesias.

*Comparisons*

The varieties most like my new variety are Freesia Marie Frazee (Plant Patent No. 609), and Freesia Snowstorm (Plant Patent No. 487).

My new variety differs from Marie Frazee as follows:

1. The color of my variety is white with cream overcast and with a very distinct vivid yellow throat and petal splotch, while the color of Marie Frazee is pure white, with a touch of soft yellow in the throat.

2. The flower of my variety has a very tubular shape, while the flowers of Freesia Marie Frazee are more funnel shaped and much shorter.

3. The stamens of my variety are pure white as contrasted with those of Marie Frazee which are greenish-white with yellow anthers.

4. The pistils of my variety are prominent while those of Marie Frazee are small and inconspicuous.

5. The flowers of my variety are larger, longer and set farther apart on the spike than those of Marie Frazee, which gives them a less crowded appearance.

My new variety differs from Snowstorm as follows:

1. The color of my variety is white overcast with cream and with a splotch and throat of vivid deep yellow, while the color of Snowstorm is waxy white with a very slight tint of lavender on the outer surface and a very slight yellow splotch.

2. The yellow splotch of my flower is much more outstanding.

3. The flower stems of my variety are much taller than those of Snowstorm when grown under similar conditions.

4. The growth of my variety is more vigorous and taller than those of Snowstorm when grown under similar conditions.

5. The flower of my variety is larger when grown under similar conditions.

6. Stems of my variety are thicker and more rigid than those of Snowstorm.

Having thus disclosed my invention, I claim:

The new and useful variety of giant type freesia plant substantially as herein shown and described, characterized particularly by the new combination of qualities including its healthy vigorous growth; its thick, rigid, long stems; its early blooming season; its very fragrant, wide-open flowers of heavy texture and unusually good keeping qualities; and the cream overcast and vivid yellow throat and splotch of its primarily white flowers.

CORNELIUS JOHN VAN BOURGONDIEN.